United States Patent [19]

Megerle et al.

[11] Patent Number: 5,730,942
[45] Date of Patent: Mar. 24, 1998

[54] APPARATUS FOR MEASURING THE CONTENT OF FOREIGN SUBSTANCES IN A GAS STREAM

[75] Inventors: Walter Megerle, Pforzheim; Klaus Moessinger, Obersulm; Gerhard Tritt, Effringen, all of Germany

[73] Assignee: Filterwerk Mann & Hummel GmbH, Ludwigsburg, Germany

[21] Appl. No.: 573,780

[22] Filed: Dec. 18, 1995

[30] Foreign Application Priority Data

Dec. 17, 1994 [DE] Germany .................. 44 45 102.4

[51] Int. Cl.⁶ ........................................ G01M 27/00
[52] U.S. Cl. ............... 422/82.01; 422/68.1; 422/82.02; 422/83; 422/95; 422/96; 422/98; 204/408; 204/409; 204/424; 73/31.03; 73/61.43; 73/61.71; 73/863.41; 73/863.51; 73/863.58; 73/863.61; 73/863.71; 73/863.84; 73/864.81; 374/147; 374/148
[58] Field of Search .................. 422/68.1, 82.01, 422/82.02, 83, 98, 95, 96; 204/408, 409, 424; 73/31.03, 61.43, 61.71, 863.41, 863.51, 863.61, 863.58, 863.71, 863.84, 864.81; 374/147, 148

[56] References Cited

U.S. PATENT DOCUMENTS

| | | | |
|---|---|---|---|
| 3,901,672 | 8/1975 | Roberts | 73/864.81 |
| 4,115,229 | 9/1978 | Capone | 73/863.61 |
| 4,131,011 | 12/1978 | Ling | 73/863.61 |
| 4,165,630 | 8/1979 | Felder et al. | 73/31.03 |
| 4,170,455 | 10/1979 | Henrie | 422/83 |
| 4,336,329 | 6/1982 | Hesse et al. | 435/286.1 |
| 4,339,318 | 7/1982 | Tanaka et al. | 204/408 |
| 4,401,967 | 8/1983 | Miwa et al. | 422/98 |
| 4,443,791 | 4/1984 | Risgin et al. | 422/98 |
| 4,459,266 | 7/1984 | Lamoreaux | 422/86 |
| 4,522,218 | 6/1985 | Konek | 73/863.61 |
| 4,538,794 | 9/1985 | Scherff | 266/79 |
| 4,548,517 | 10/1985 | Kampmann | 374/143 |
| 4,823,803 | 4/1989 | Nakamura | 128/717 |
| 5,017,340 | 5/1991 | Pribat et al. | 422/68.1 |
| 5,042,288 | 8/1991 | Vig | 73/24.001 |
| 5,057,436 | 10/1991 | Ball | 436/113 |
| 5,115,687 | 5/1992 | Clingman, Jr. et al. | 73/863.61 |

(List continued on next page.)

FOREIGN PATENT DOCUMENTS

| | | | |
|---|---|---|---|
| 2713622 | 10/1978 | Germany . | |
| 3046081 | 7/1982 | Germany . | |
| 3707622 | 9/1988 | Germany . | |
| 3808305 | 9/1989 | Germany . | |
| 4031430 | 1/1992 | Germany . | |
| 4223432 | 2/1993 | Germany . | |
| 4210397 | 10/1993 | Germany . | |
| 0199144 | 8/1989 | Japan | 73/31.03 |
| 2187286 | 9/1987 | United Kingdom . | |
| 2203247 | 10/1988 | United Kingdom . | |

OTHER PUBLICATIONS

Abstract of Published Japanese Patent Application No. JP 01-127,944. May 19, 1989.

*Primary Examiner*—Robert J. Warden
*Assistant Examiner*—Sharidan Carrillo
*Attorney, Agent, or Firm*—Evenson, McKeown, Edwards & Lenahan P.L.L.C.

[57] ABSTRACT

A system for measuring the content of foreign substances in a gas stream, for example oil in a stream of compressed air. The system includes at least one probe for collecting a given amount of gas. In the probe there is at least one sensor over which the sampled gas is passed. For optimum evaluation and for signaling certain states of operation, the sensor includes a temperature sensor for determining the temperature of the gas sample flowing past it, and a detector whose electrical resistivity or conductivity depends on the nature and density of the foreign substances in the gas. The output signal of the detector corresponds to the concentration of foreign substance in the gas stream, and is processed in an electronic evaluation unit.

19 Claims, 1 Drawing Sheet

U.S. PATENT DOCUMENTS

| | | | |
|---|---|---|---|
| 5,138,869 | 8/1992 | Tom | 73/31.03 |
| 5,292,666 | 3/1994 | Fabinski et al. | 436/114 |
| 5,325,705 | 7/1994 | Tom | 73/31.03 |
| 5,340,542 | 8/1994 | Fabinski et al. | 422/82.05 |
| 5,410,875 | 5/1995 | Tanaka et al. | 60/288 |
| 5,460,054 | 10/1995 | Tran | 73/863.61 |
| 5,486,336 | 1/1996 | Dalle Betta et al. | 422/98 |
| 5,517,182 | 5/1996 | Yasunaga | 422/98 |

APPARATUS FOR MEASURING THE CONTENT OF FOREIGN SUBSTANCES IN A GAS STREAM

BACKGROUND OF THE INVENTION

This invention relates to an apparatus for measuring the content of foreign substances in a gas steam comprising at least one probe for collecting a given amount of gas from the gas stream and at least one sensor in a measuring chamber of the probe past which the sampled amount of gas is carried.

U.S. Pat. Nos. 5,292,666 and 5,340,542 disclose a system for measuring the content of foreign substances in a gas stream. In this system a given amount of gas is fed to a sensor for determining the content especially of organic carbon in the gas. This gas sample is fed through a thermal reactor and then a modulated infrared light beam is passed through it to determine the concentration of carbon. The construction of this known system, as well as the method of measurement, which calls for an additional measuring operation with a reference gas, is relatively expensive and requires a complicated evaluation procedure.

In many applications in which a gas stream or air stream is necessary for the operation of an apparatus, for example in pneumatic systems, there is a danger that particles of oil or dirt will be entrained in the gas or air stream and will adversely affect the operation of the apparatus. Especially in cases where compressed air has a high residual oil content due to damaged parts in the air compressor system, an apparatus driven by the compressed air can also be damaged.

If such contamination is not detected and eliminated in due time, the entire compressed air supply network including the apparatus connected to it will have to be subjected to complicated and expensive cleaning. Moreover, the useful life of filters used in preparing compressed air is greatly shortened by the presence of such contamination, and the overall reliability of operation is impaired.

SUMMARY OF THE INVENTION

It is the object of the present invention to provide an improved apparatus for measuring foreign matter in a gas stream.

It is a particular object of the invention to provide an apparatus for measuring the presence of foreign matter in a gas stream which comprises at least one probe for collecting a given amount of gas from the gas stream and at least one sensor in a measuring chamber of the probe past which the sampled amount of gas is carried.

A further object of the invention is to provide an apparatus for measuring the presence of foreign matter in a gas stream which facilitates a precise measurement and easy evaluation of the measured result.

It is also an object of the invention to provide an apparatus for measuring the presence of foreign matter in a gas stream which has a flexible design.

These and other objects have been achieved in accordance with the present invention by providing an apparatus for determining a content of a foreign substance in a gas stream comprising at least one probe for collecting a sample of gas from the gas stream, the probe comprising a measuring chamber containing at least one sensor past which the collected gas sample flows, the sensor comprising a temperature sensor for measuring the temperature of the gas sample and a detector having electrical characteristics which vary depending on the foreign substance content of the gas sample, and means for receiving output signals from the temperature sensor and from the detector and for evaluating the output signals from the detector in relation to the measured temperature and a stored calibration curve.

In order to prevent the operational reliability of, for example, compressed air systems from being impaired, it is advantageous to detect foreign matter, especially oil contamination, in the air stream with a detection and warning system. In the case of so-called "residual oil indicators," therefore, a measure of the amount of oil particles in the air stream is detected and processed.

Advantageously, the system according to the invention contains a sensor whose electrical conductivity varies with the oil content of the gas stream. In addition, the temperature of the gas stream is measured with a temperature sensor, since this has an effect on the readings.

In accordance with an especially advantageous embodiment, the amount of gas required for the measurement is obtained by probes in different parts of the gas stream, since for example a higher contamination density establishes itself by gravity in the lower wall portion of a pipeline system than in the upper portion. The use of limits for the temperature of the gas stream, for example of about 50° C., assure that the reading is not distorted by hydrocarbon droplets entrained in the gas stream.

In one preferred embodiment of the invention, an advantageous aspiration of the amount of gas required for the measurement is achieved due to the vacuum that forms at the mouth of the probe, and a relatively slower gas stream is established in the measuring chamber in comparison to the main gas stream. The sensors used in the apparatus of the invention can be semiconductor gas sensors, tin oxide gas sensors, quartz sensors or piezoceramic sensors. The required reactions of the sensors lead with greater reliability to useful measured readings.

Other preferred embodiments of the apparatus according to the invention in which the measured values are conditioned, processed, and transferred to an electronic interface, such as a controller for example, particularly by means of a microprocessor, permit any exceeding of the limits to be signaled in a simple manner. The use of a microprocessor, in conjunction with software that automatically establishes parameters, permits a maximum adaptability to various operating conditions and types of apparatus.

It is especially advantageous if the foreign substance content in the gas stream is detected under different conditions of operation.

BRIEF DESCRIPTION OF THE DRAWINGS

The invention will be described in further detail hereinafter with reference to illustrative preferred embodiments depicted in the accompanying drawings in which.

DETAILED DESCRIPTION OF PREFERRED EMBODIMENTS

Figure 1:
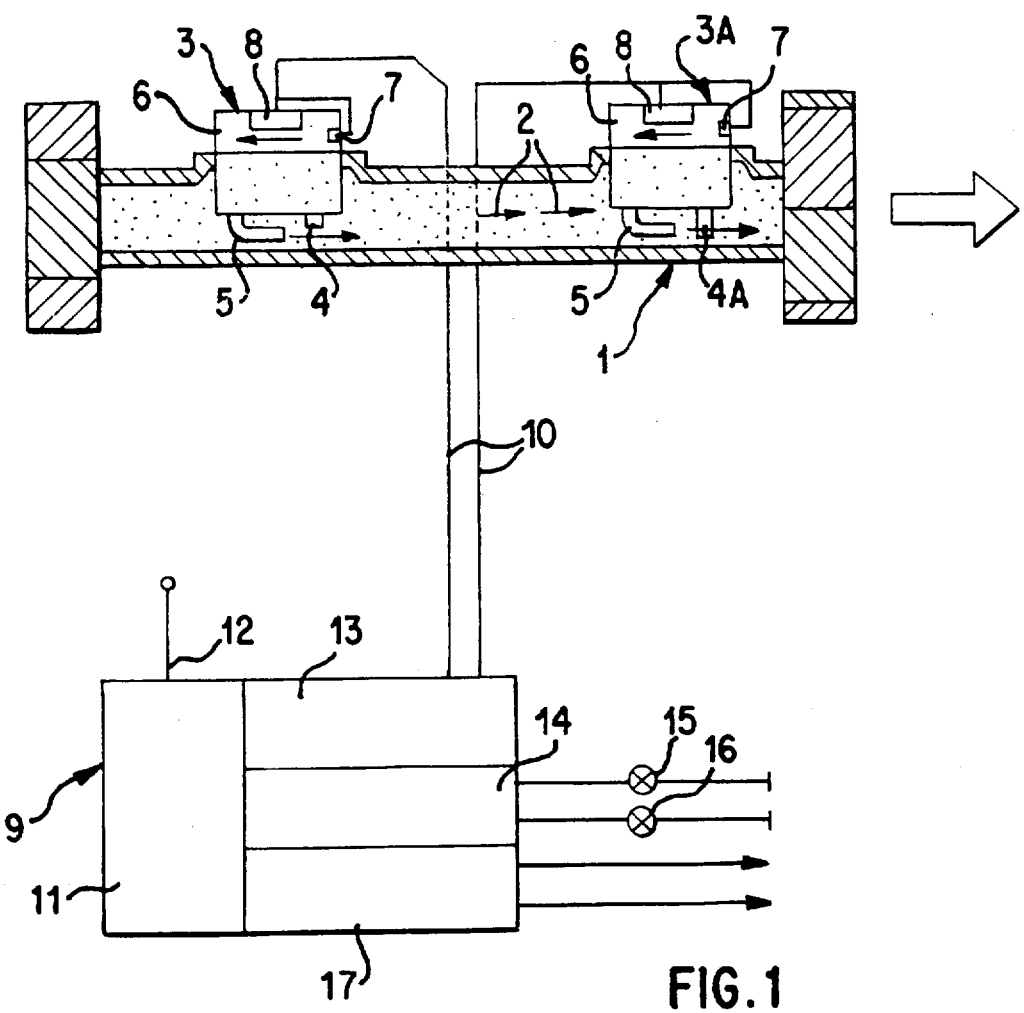
FIG. 1 is a sectional view taken through a pipe system for supplying compressed air comprising a sensor module and a processing unit.

FIG. 1 shows a section of the supply line system 1 of a gas supply, such as a compressed air supply network, which carries a compressed-air stream indicated by arrows 2 in the interior of the pipe or duct. A probe 3 is mounted at a given point in the supply line system 1, for example by means of threaded screws. The probe 3 has an inlet 4 and an outlet 5 for a specific amount of gas. A sample of the gas flowing through the supply line is aspirated into the probe 3 by means of the vacuum generated by the flow of the gas stream 2 past outlet 5.

In the illustrated embodiment, the amount of gas required for the measurements is collected from the bottom area of the supply line, since, due to the force of gravity, it is here that the greatest concentration of foreign matter can be expected. However, it is conceivable that the sample to be measured could be collected from in other areas of the supply line. Optionally, a combination of several probes 3,3A positioned in different areas may be used to increase the accuracy of the measurement. FIG. 1 shows two probes 3,3A for collecting gas samples from the gas stream. Probe 3 has an inlet 4 reaching into a central region of the gas stream between a top wall and a bottom wall of a supply line in which the gas stream is carried. Probe 3A has an inlet 4A which reaches into a lower region of the gas stream adjacent a bottom wall of the supply line in which the gas stream is carried.

In the upper part of the probe 3 there is a sensor 6 which contains a temperature sensor 7 and a detector 8 for measuring the foreign matter. As the gas sample flows past the detector 8, the conductivity of the detector material will vary in accordance with the electrical properties of the detector 8, depending on the chemical composition of the gas sample. Commercially available semiconductor detectors which undergo a change in resistance between at least two terminal poles when, for example, a gas sample containing oil passes over their surface, can be used as detectors. In particularly preferred embodiments the detector 8 may be a semiconductor sensor or a tin oxide sensor with a catalytic oxidation and corresponding variation of the electrical conductivity or resistance according to the foreign substance concentration in the gas stream. Based on the output signal of the temperature sensor 7, the electrical signal obtained with the change of conductivity or resistance can be processed in an evaluating unit 9.

It is also possible to use quartz or piezoceramic sensors. In such a case, the sensor is a component of an electrical oscillating circuit the characteristic frequency of which is adjusted depending on the foreign substance content of the gas or whose value varies according to the foreign substance content.

A signal line 10 produces a connection between the probe 3 and an evaluating unit 9, which as a rule is disposed at a central location. The probes 3, the detector 8 and the temperature sensor 7 preferably are combined together as a measuring module which can be screwed into prepared openings into the supply line system 1 carrying the gas stream and preferably are connected by plug-in signal lines 10 to the processing unit 9. The evaluating unit 9 comprises a power supply 11 which is connected with a source of electrical power, for example a mains voltage, in a conventional manner not explicitly shown in the drawing. The operational state, i.e. the on-off state, of the compressor which supplies the compressed air is signaled to the evaluating unit 9 through a signal line 12.

The evaluating unit furthermore comprises an interface 13 for processing the output signal from the probe and transmitting it to a microprocessor 14. Signaling devices 15 and 16 can be connected to outputs from the microprocessor to warn, for example, that various measurements have exceeded preset limits. Thus, for example, a first signal can indicate the need for replacement of a filter, and a second signal can be a shut-off signal. Also, direct signals for control or regulating systems affecting the compressed-air supply network can be produced via an interface 17.

Figure 2:
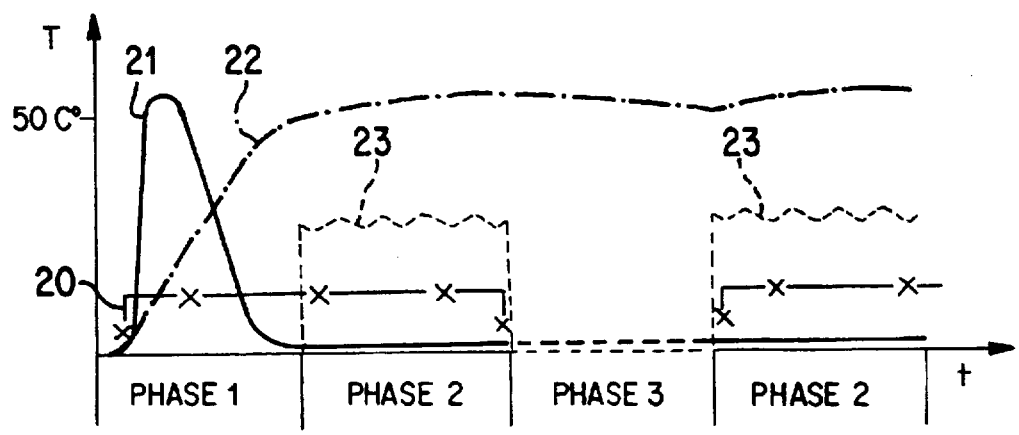
FIG. 2 is a graphic representation of various phases of measurement.

FIG. 2 depicts the course of the different conditions and measured values over a period of time t in the operation of the embodiment described above. Line 20 indicates the actuation and deactivation of the air compressor starting in phase 1. After the compressor starts, the water content or humidity of the compressed air indicated by line 21 becomes sharply perceptible and then declines. The temperature T of the compressed air increases along a line 22 up to a level above about 50° C. and thus begins phase 2. During this phase 2 the foreign substance content (in this case residual oil) in the gas sample is detected in the probe 3 as represented by line 23. These readings are integrated over time t. In phase 3 a compressor shut-off follows, with a gradual lowering of the temperature. When the compressor turns on again in the next following phase 2, the temperature T again exceeds the level of 50° C., and another measurement cycle can begin as described above.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An apparatus for determining a content of a foreign substance in a gas stream, said apparatus comprising at least a first probe and a second probe for collecting gas samples from the gas stream, each of said probes having a measuring chamber containing at least one sensor past which the collected gas sample flows, said sensor comprising a temperature sensor for measuring the temperature of the gas sample and a detector having electrical characteristics which vary depending on the foreign substance content of the gas sample, said first probe having an inlet reaching into a central region of the gas stream between a top wall and a bottom wall of a supply line in which the gas stream is carried, and said second probe having an inlet which reaches into a lower region of said gas stream adjacent said bottom wall of the supply line in which the gas stream is carried, and means for receiving output signals from said temperature sensor and from said detector and for evaluating the output signals from the detector and the temperature sensor in order to determine the foreign substance content of the gas stream.

2. An apparatus according to claim 1, wherein the gas stream is compressed air and the foreign substance is oil or an oil-containing substance.

3. An apparatus according to claim 2, wherein the collected gas sample is heated in each of said probes to a temperature of at least about 50° C., and the output signals from the detector are evaluated only when the temperature of the gas sample is above about 50° C.

4. An apparatus for determining a content of a foreign substance in a gas stream, said apparatus comprising at least one probe for collecting a sample of gas from the gas stream, said probe comprising a measuring chamber containing at least one sensor past which the collected gas sample flows and a measuring chamber outlet past which the gas stream flows such that a vacuum is produced in the outlet sufficient to aspirate the gas sample through a probe inlet into the measuring chamber, said sensor comprising a temperature sensor for measuring the temperature of the gas sample and a detector having electrical characteristics which vary depending on the foreign substance content of the gas sample, and means for receiving output signals from said temperature sensor and from said detector and for evaluating the output signals from the detector and the temperature sensor in order to determine the foreign substance content of the gas stream.

5. An apparatus according to claim 4, wherein said outlet is bent so that it opens in the direction in which the gas stream flows.

6. An apparatus according to claim 1, wherein the detector and the temperature sensor of each said probes are combined into a modular assembly which can be mounted as a unit on a supply line for a gas stream in which foreign substances are to be measured.

7. An apparatus according to claim 6, wherein the detector and the temperature sensor are connected by signal lines to said evaluating means, and wherein said signal lines can be plugged into said modular assembly.

8. An apparatus according to claim 1, wherein the detector comprises a semiconductor gas sensor which effects catalytic oxidation of foreign substances in the gas stream, said semiconductor gas sensor having an electrical resistance which varies in accordance with the amount of foreign substance catalytically oxidized thereon.

9. An apparatus according to claim 1, wherein the detector comprises a tin oxide gas sensor which effects catalytic oxidation of foreign substances in the gas stream, said tin oxide gas sensor having an electrical resistance which varies in accordance with the amount of foreign substance catalytically oxidized thereon.

10. An apparatus according to claim 1, wherein the detector comprises a quartz sensor or a piezoceramic sensor of an electrical oscillator circuit having a characteristic frequency which varies depending on the foreign substance content of the gas stream.

11. An apparatus according to claim 1, further comprising a signaling device for indicating when the gas sample contains a concentration of foreign substance exceeding a preset limit value.

12. An apparatus according to claim 2, wherein the evaluating means comprises a microprocessor programmed to determine the foreign substance concentration of the gas stream under given operating conditions of a system in which the gas stream is produced.

13. An apparatus according to claim 12, wherein said gas stream is a stream of compressed air.

14. An apparatus according to claim 2 wherein the evaluating means comprises a microprocessor programmed to determine the foreign substance concentration of the gas stream under given operating conditions of a system in which the gas stream is produced, and wherein in a first phase of operation, the apparatus is started without evaluation of the detector output signal;

in a second phase of operation beginning when a predetermined operating temperature is attained, the detector output signal is evaluated to determine the foreign substance content of the gas stream, and the detector output signal is stored, and in a third phase of operation, the detector output signal is again not evaluated.

15. An apparatus according to claim 1, wherein the evaluating means comprises a microprocessor programmed to determine the foreign substance concentration of the gas stream under given operating conditions of a system in which the gas stream is produced, wherein in a first phase of operation, the apparatus is started without evaluation of the detector output signal;

in a second phase of operation beginning when a predetermined operating temperature is attained, the detector output signal is evaluated to determine the foreign substance content of the gas stream, and the detector output signal is stored, and in a third phase of operation, the detector output signal is again not evaluated;

and wherein said apparatus is a compressed air system comprising a compressor for producing compressed air, and the compressor is deactivated to begin the third phase of operation.

16. An apparatus according to claim 1, wherein said means for evaluating the output signals determines the foreign substance content of the gas stream from a stored calibration curve as a function of the output signals from the temperature sensor and the detector.

17. An apparatus according to claim 1, wherein said collected gas sample flows through said measuring chamber at a slower speed than a speed of the gas stream in the supply line.

18. An apparatus according to claim 1, wherein said collected gas sample flows through said measuring chamber in a direction opposite to a direction of flow of the gas stream in the supply line.

19. An apparatus according to claim 6, wherein said collected gas sample flows through said measuring chamber in a direction opposite to a direction of flow of the gas stream in the supply line.

* * * * *